(12) United States Patent
Zhang et al.

(10) Patent No.: US 10,308,932 B2
(45) Date of Patent: Jun. 4, 2019

(54) METHOD FOR EXPRESSING, SECRETING AND TRANSFERRING FUNCTIONAL MICRORNAS/SIRNAS AND APPLICATION THEREOF

(71) Applicant: MICROMEDMARK BIOTECH CO., LTD., Beijing (CN)

(72) Inventors: Chenyu Zhang, Beijing (CN); Ke Zeng, Beijing (CN)

(73) Assignee: MICROMEDMARK BIOTECH CO., LTD., Beijing (CN)

( * ) Notice: Subject to any disclaimer, the term of this patent is extended or adjusted under 35 U.S.C. 154(b) by 0 days.

(21) Appl. No.: 14/410,492

(22) PCT Filed: Jun. 21, 2013

(86) PCT No.: PCT/CN2013/077705
§ 371 (c)(1),
(2) Date: Dec. 22, 2014

(87) PCT Pub. No.: WO2013/189309
PCT Pub. Date: Dec. 27, 2013

(65) Prior Publication Data
US 2016/0017321 A1    Jan. 21, 2016

(30) Foreign Application Priority Data
Jun. 21, 2012    (CN) .......................... 2012 1 0212690

(51) Int. Cl.
| | | |
|---|---|---|
| C07H 21/04 | (2006.01) |
| C12N 15/113 | (2010.01) |
| C12N 15/11 | (2006.01) |
| A61K 31/7105 | (2006.01) |
| A61K 31/713 | (2006.01) |
| C12N 15/87 | (2006.01) |
| C12N 15/88 | (2006.01) |
| A61K 48/00 | (2006.01) |

(52) U.S. Cl.
CPC .......... *C12N 15/113* (2013.01); *A61K 31/713* (2013.01); *A61K 31/7105* (2013.01); *C12N 15/111* (2013.01); *C12N 15/87* (2013.01); *C12N 15/88* (2013.01); *A61K 48/0075* (2013.01); *C12N 2310/14* (2013.01); *C12N 2310/141* (2013.01); *C12N 2320/32* (2013.01); *C12N 2320/35* (2013.01)

(58) Field of Classification Search
CPC ...................................................... A61K 48/00
USPC ........................................................ 536/24.5
See application file for complete search history.

(56) References Cited

U.S. PATENT DOCUMENTS

| | | | | |
|---|---|---|---|---|
| 2010/0041737 A1* | 2/2010 | Naldini | ............... | C12N 15/635 |
| | | | | 514/44 R |
| 2011/0009469 A1* | 1/2011 | Mendell | ............... | A61K 31/145 |
| | | | | 514/44 A |
| 2013/0259926 A1* | 10/2013 | Rao | .................... | C12N 15/1138 |
| | | | | 424/450 |

FOREIGN PATENT DOCUMENTS

| | | |
|---|---|---|
| CN | 101386848 | 3/2009 |
| CN | 101869715 | 10/2010 |
| CN | 102218144 | 10/2011 |
| WO | 2009/046059 | 4/2009 |
| WO | 2012/071648 | 6/2012 |

OTHER PUBLICATIONS

Valadi et al. Nature Cell Biology vol. 9, Jun. 2007: 654-659).*
Sachdeva et al. (Am J Transl Res 2010;2(2):170-180).*
Michael et al. (Molecular Cancer Research vol. 1, 882-891, Oct. 2003).*
Kerscher et al. (Nature Reviews vol. 6, 2006; 259-269).*
Extended European search report for European application No. 13807063.6, dated Feb. 22, 2016 (11 pages).
S. David et al., "Non-viral nanosystems for systemic siRNA delivery," Pharmacological Research, vol. 62 (2010), p. 100-114.
A. F. Ibrahim et al., "MicroRNA Replacement Therapy for miR-145 and miR-33a Is Efficacious in a Model of Colon Carcinoma," Cancer Research, vol. 71, No. 15 (2011), p. 5214-5224.
J. Nguyen and F. C. Szoka, "Nucleic Acid Delivery: The Missing Pieces of the Puzzle?," Accounts of Chemical Research, vol. 45, No. 7 (2012), p. 1153-1162.
Y.K. Oh and T G. Park, "siRNA delivery systems for cancer treatment," Advanced Drug Delivery Reviews, vol. 61 (2009) p. 850-862.
Q. Pan et al., "Hepatic cell-to-cell transmission of small silencing RNA can extend the therapeutic reach of RNA interference (RNAi)," Gut, vol. 61 (2012), p. 1330-1339.
F. M. van de Water et al., "Intravenously administered short interfering RNA accumulates in the kidney and selectively suppresses gene function in renal proximal tubules," Drug Metabolism and Disposition, vol. 34, No. 8 (2006), p. 1393-1397.

(Continued)

*Primary Examiner* — Kimberly Chong
(74) *Attorney, Agent, or Firm* — Hamre, Schumann, Mueller & Larson, P.C.

(57) ABSTRACT

The present invention relates to a microparticle comprising a functional microRNA/siRNA and application thereof. Specifically, disclosed is a use of a functional microRNA and/or siRNA, which is used to prepare a composition applied to a mammal. After the composition is applied, the microparticle is formed in a first part in an animal, and transported to a second part, which thereby improves physiological status of the second part or heals a disease of the second part. The second part is different from the first part. The use is beneficial for optimizing a dosing manner of the functional microRNA and/or siRNA.

2 Claims, 6 Drawing Sheets

(56) References Cited

OTHER PUBLICATIONS

T. Viel et al., "Molecular Imaging Study on In Vivo Distribution and Pharmacokinetics of Modified Small Interfering RNAs (siRNAs)," Oligonucleotides, vol. 18 (2008), p. 201-212.
J. Wang et al., "Delivery of siRNA Therapeutics: Barriers and Carriers," The AAPS Journal, vol. 12, No. 4 (2010), p. 492-503.
Y. Zhang et al., "Secreted Monocytic miR-150 Enhances Targeted Endothelial Cell Migration," Molecular Cell, vol. 39 (2010), p. 133-144.
International Search Report of PCT/CN2013/077705, dated Sep. 29, 2013, 10 pages total (English translation provided).

\* cited by examiner

METHOD FOR EXPRESSING, SECRETING AND TRANSFERRING FUNCTIONAL MICRORNAS/SIRNAS AND APPLICATION THEREOF

FIELD OF THE INVENTION

The present invention belongs to the field of medicine, particularly relates to the new application of functional microRNA/siRNA, and more particularly relates to cell microvesicles containing functional microRNA/siRNA and application thereof.

BACKGROUND ART

Micro-ribonucleic acids microRNAs (microRNA) are a type of single-stranded small ribonucleic acid molecules with a length of about 19-23 nucleotides; they are located at the non-coding region of a genome and evolutionarily highly conserved, and can regulate the gene expression by inhibiting the translation process of target genes and are closely related to many normal physiological activities of animals, such as the individual development, tissue differentiation, cell apoptosis, and energy metabolism of organisms, and meanwhile are closely associated with the occurrence and development of many diseases. Since lin-4 and let-7, which are involved in the regulation of the timing development of nematodes, have been found, microRNA has gradually become the research hotspot with respect to the regulation of mRNA stability and protein translation, which was chosen as one of the ten annual scientific breakthroughs by journal *Science* two times in 2002 and 2003, respectively. It is now predicted that microRNA can regulate at least 5300 human genes, that is, 30% of all of the genes. As the research moves along, more and more microRNAs are found, in which the relationship between microRNAs and tumor becomes gradually the focus of research, and it has been found that several microRNAs are highly related to chronic lymphocytic leukemia, lung cancer, breast cancer, and colon cancer by negatively regulating the expression of genes.

Small interfering ribonucleic acids (small interfering RNA, siRNA) are a type of double-stranded RNA molecules composed of more than 20 nucleotides, which can exert the effect of silencing gene expression by specifically degrading the messenger ribonucleic acids (messenger RNA, mRNA) of target genes. This process is called RNA interference, RNAi.

RNA interference is a mode of post-transcriptional regulation of genes. SiRNA can specifically recognize target genes thereof and can recruit a protein complex which is called silencing complex (RNA induced silencing complex, RISC). RISC comprises ribonuclease and the like, which can specifically and efficiently inhibit the expression of genes through the manner of targeted cleaving homologous mRNA. Since the use of RNA interference technology can specifically knock out or shut down the expression of particular genes, this technology has been widely used in the fields of biomedical experimental research and therapy of various diseases.

MicroRNA and siRNA Involved in the Therapy of Diseases

Current studies have proved that the progress of diseases can be interrupted or delayed through regulating the content of particular microRNAs in the body of an organism or through injecting exogenous siRNA. They both can participate in the treatment and prevention of diseases through affecting the expression of particular proteins. For instance, the expression of miR-206 in skeletal muscles can relieve the injury or loss of motor neurons, the effect of which is mainly realized by promoting and activating the generation of links of neurons between muscles, thus treating amyotrophic lateral sclerosis (also called ALS); and down-regulation of the expression of miR-122 in liver can exert therapeutic effects on hepatitis C; and since the overexpression of Bcl-2 resulted by the loss of miR-15 and miR-16 is an important mechanism for the occurrence of human chronic lymphatic leukemia (CLL), the overexpression of miR-15 and miR-16 in organisms can exert therapeutic effects on CLL.

Although there are many achievements on the study and development of microRNA and siRNA, many problems still exist before their practical application as pharmaceuticals in medical treatment, especially how to improve the efficiency of delivering such pharmaceuticals; and in general their efficacy can be exerted only when administration at a focus site is required, but this therapeutic method of in situ administration severely limits the application of the pharmaceuticals.

CONTENTS OF THE INVENTION

One of the objects of the present invention is to provide a use of a functional microRNA and/or siRNA for preparing a composition to be applied to mammals, said composition forms cell microvesicles at a first site in the body of an animal and is delivered to a second site so as to improve a physiological state at the second site or treat a disease at the second site, in which the second site is different from the first site.

Another object of the present invention is to provide an ex situ therapeutic method, said method comprises the step of applying at a first site a microRNA and/or siRNA to a subject in need of treatment, so as to treat a disease at a second site. Said method facilitates the diversification of administration modes, overcomes the difficulty of inconvenience for administration at certain sites, and facilitates seeking for an administration mode which is mostly suitable for the subject to be treated.

In a first aspect of the present invention, provided is a use of a functional microRNA and/or siRNA for preparing a composition to be applied to mammals; said composition forms cell microvesicles at a first site in the body of an animal and is delivered to a second site so as to improve a physiological state at the second site or treat a disease at the second site, in which the second site is different from the first site.

In a second aspect of the present invention, provided is a use of a functional microRNA and/or siRNA for preparing a composition to be applied to mammals, said composition forms cell microvesicles at a first site in the body of an animal and is delivered to a second site so as to regulate the expression of the target genes of the functional microRNA and/or siRNA at the second site, in which the second site is different from the first site.

In another preferred example, said target genes include MYC, K-ras, CCND2, cdk6, E2F3, MEK2, ERK5, PTGS2, and DFF45.

In another preferred example, said site includes cell, tissue and/or organ.

In another preferred example, said first site is far from the second site.

In another preferred example, provided is a use of a functional microRNA and/or siRNA enclosed by cell microvesicles for preparing a composition for treating the disease at a site which is not the generating place of said microvesicles.

In another preferred example, said functional microRNA is an animal microRNA or an expression vector thereof, a plant microRNA or an expression vector thereof, or a microbial microRNA or an expression vector thereof, or a combination thereof; or said functional microRNA is a natural microRNA or an expression vector thereof, an artificially synthesized microRNA or an expression vector thereof, or a combination thereof;

Said functional siRNA is an animal siRNA or an expression vector thereof, a plant siRNA or an expression vector thereof, or a microbial siRNA or expression vector thereof, or a combination thereof; or said functional siRNA is a natural siRNA or an expression vector thereof, an artificially synthesized siRNA or an expression vector thereof, or a combination thereof.

In another preferred example, said expression vector includes a plasmid vector, an adenovirus vector, a lentiviral vector, a retroviral vector or an inducible expression vector.

In another preferred example, said first site includes liver, lung, gastrointestinal tract, mammary gland, kidney, brain, spleen, lymph, thyroid, reproductive organ, blood cells or lymphocytes; and/or Said second site includes brain, pineal body, pituitary body, eye, ear, nose, mouth, pharynx, parotid gland, tonsil, esophagus, trachea, thyroid, thymus, mammary gland, lung, heart, stomach, intestines, appendix, liver, gallbladder, spleen, pancreas, kidney, ureter, bladder, urethra, uterus, ovary, fallopian tube, vagina, spermatic duct, prostate, penis, testis, anus, bone, muscle, connective tissue, nerves, lymph, colorectum, blood, bone marrow, or skin.

In another preferred example, said first site includes liver, lung, gastrointestinal tract, kidney, blood cells, or lymph.

In another preferred example, said disease includes those diseases specifically related to a functional microRNA and/or siRNA, including (but not limited to) tumors, acute and chronic infectious diseases or other acute and chronic diseases.

In another preferred example, said acute and chronic infectious diseases include virus influenza, virus hepatitis, acquired immunodeficiency syndrome, viral diseases such as SARS, bacterial diseases (for example tuberculosis, bacterial pneumonia), and other acute and chronic infectious diseases caused by various pathogenic microorganisms;

In another preferred example, said other acute and chronic diseases include respiratory system diseases, immune system diseases, blood and hematopoietic system diseases (such as circulatory diseases including cardiovascular and cerebrovascular diseases), metabolic diseases related to endocrine system, digestive system diseases, nervous system diseases, urinary system diseases, reproductive system diseases and motor system diseases.

In another preferred example, the application mode of said composition includes oral, respiratory tract, injection, transdermal, mucosal, or cavity administration.

In a third aspect of the present invention, provided is a preparation method of cell microvesicles, which comprises the step of applying a functional microRNA and/or siRNA to a mammal and allowing internalization of said functional microRNA and/or siRNA, whereby said functional microRNA and/or siRNA is enclosed at a certain site of said mammal to form cell microvesicles.

In another preferred example, said cell microvesicles are releasable and can be delivered to another site.

In another preferred example, said application mode includes oral, respiratory tract, injection, transdermal, mucosal, and cavity administration.

In another preferred example, said site includes cells, tissues and/or organs.

In another preferred example, said certain site is the first site described in the present invention.

In another preferred example, said another site is the second site described in the present invention.

In the fourth aspect of the present invention, provided is a pharmaceutical composition which comprises (1) a pharmaceutically acceptable carrier; and (2) a functional microRNA and/or siRNA; in which said microRNA and/or siRNA is enclosed at a certain site of a mammal after it is applied to said mammal so as to form cell microvesicles.

In another preferred example, said site includes cells, tissues and/or organs.

In another preferred example, said cell microvesicles can be delivered to another site and exert its function at said another site.

In another preferred example, said certain site is the first site described in the present invention.

In another preferred example, said another site is the second site described in the present invention.

In another preferred example, said pharmaceutical composition includes a tablet, a capsule, a powder, a pill, a granule, a syrup, a solution, a suspension liquid, an emulsion, a suspension, a spray, an aerosol, a powder spray, a volatile liquid, an injection, a powder for injection, a topical solution, a lotion, a pour agent, a liniment, a cataplasma, a medicinal paste, a rubber paste, an ointment, a plaster, a paste, an eye drop, a nasal drop, an ophthalmic ointment, a mouth wash, a sublingual tablet, or a suppository.

In a fifth aspect of the present invention, provided is a therapeutic method, which comprises the step of applying at a first site with a functional microRNA and/or siRNA to a subject in need of treatment so as to treat a disease at a second site, in which the second site is different from the first site.

In another preferred example, said method comprises the step of applying at a first site a functional microRNA and/or siRNA to a subject in need of treatment, said microRNA and/or siRNA are taken in and enclosed to form cell microvesicles which are delivered to a second site, thereby treating a disease at the second site.

In another preferred example, the application mode of said functional microRNA and/or siRNA includes oral, respiratory tract, injection, transdermal, mucosal, or cavity administration.

In another preferred example, said first site is far from the second site.

In another preferred example, said second site is a focus site.

In a sixth aspect of the present invention, provided is a therapeutic method, which comprises the step of applying the pharmaceutical composition described in the fourth aspect of the present invention to a subject in need of treatment so as to treat the disease of said subject.

In another preferred example, said subject in need of treatment includes human.

In another preferred example, said disease include those diseases specifically related to a functional microRNA and/or siRNA, including (but not limited to) tumors, acute and chronic infectious diseases or other acute and chronic diseases, in which said acute and chronic infectious diseases include virus influenza, virus hepatitis, acquired immunodeficiency syndrome, viral diseases such as SARS, bacterial diseases (for example tuberculosis, bacterial pneumonia), and other acute and chronic infectious diseases caused by various pathogenic microorganisms; and said other acute and chronic diseases include respiratory system diseases, immune system diseases, blood and hematopoietic system diseases (such as circulatory diseases including cardiovascular and cerebrovascular diseases), metabolic diseases related to endocrine system, digestive system diseases, nervous system diseases, urinary system diseases, reproductive system diseases and motor system diseases;

In another preferred example, said disease includes digestive system diseases (such as liver cancer) or circulatory diseases (such as lymph cancer).

It should be understood that all of the various technical features described above and hereinafter (such as examples) can be combined with one another within the scope of the present invention, so as to form new or preferred technical solutions. Due to space limitations, these are no longer tired out one by one.

DESCRIPTION OF DRAWINGS

Among them, there are four groups of data, at 6 h, 12 h, 18 h and 24 h respectively, both in FIGS. 3A and 3B; each group being composed of 5 histograms, from the left to the right, the histograms of each group represent sequentially Normal, Ad-control, Control plasmid, Ad-miR-145 and miR-145 plasmid, respectively.

PREFERRED EMBODIMENTS OF THE INVENTION

The inventors have through in-depth research unexpectedly found a therapeutic method of administering a microRNA and/or siRNA at a non-focus site (or far from a focus site) to realize the treatment of a disease at the focus site. Said method facilitates the diversification of administration modes for treating certain diseases, which is more beneficial for seeking for an administration mode best for a patient. The present invention is accomplished on this basis.

Functional microRNAs or siRNAs Described in the Present Invention

The functional microRNAs described in the present invention may include the microRNAs of various species, for instance, including functional microRNAs of animals, plants or microbes (such as miR-143, miR-145, miR-1302, miR-6723, miR-200b, miR-200a, miR-429, miR-4251, miR-551a, miR-4417, miR-4689, miR-4252, miR-34a, miR-5697, miR-1273d, miR-4632, miR-3675, miR-3972, miR-4695, miR-1290, miR-6084, miR-1256, miR-4418, miR-6127, miR-4684, miR-4253, miR-3115, miR-4419a, miR-378f, miR-4425, miR-3917, miR-1976, miR-4420, miR-4254, miR-5585, miR-3605, miR-552, miR-4255, miR-5581, miR-3659, miR-30e, miR-30c-1, miR-6079, miR-5584, miR-4421, miR-761, miR-6500, miR-1273f, miR-5095, miR-1273g, miR-4781, miR-4422, miR-4711, miR-3116, miR-6068, miR-4794, miR-3671, miR-101, miR-3117, miR-1262, miR-186, miR-4423, miR-760, miR-378g, miR-2682, miR-137, miR-553, miR-197, miR-4256, miR-548a, miR-942, miR-320b, miR-3118, miR-6077, miR-5087, miR-4257, miR-554, miR-5698, miR-190b, miR-4258, miR-92b, miR-555, miR-9, miR-765, miR-4259, miR-5187, miR-4654, miR-556, miR-3658, miR-921, miR-1255b, miR-557, miR-3119, miR-1295a, miR-1295b, miR-214, miR-3120, miR-199a, miR-488, miR-4424, miR-3121, miR-4426, miR-1278, miR-4735, miR-181b, miR-181a, miR-5191, miR-1231, miR-135b, miR-29c, miR-29b, miR-205, miR-4260, miR-3122, miR-215, miR-194, miR-664a, miR-4762, miR-5008, miR-3620, miR-4666a, miR-1182, miR-4427, miR-4671, miR-4753, miR-1537, miR-4428, miR-3123, miR-4677, miR-3916, miR-3124, miR-5699, miR-6072, miR-6078, miR-3155a, miR-3155b, miR-548a, miR-4480, miR-4481, miR-548q, miR-4293, miR-1265, miR-511, miR-4675, miR-1915, miR-1254, miR-603, miR-604, miR-938, miR-3611, miR-4683, miR-5100, miR-3156, miR-4294, miR-605, miR-548f, miR-3924, miR-1296, miR-4676, miR-606, miR-346, miR-4678, miR-4679, miR-107, miR-3157, miR-5686, miR-607, miR-1287, miR-4685, miR-6507, miR-608, miR-3158, miR-146b, miR-1307, miR-936, miR-609, miR-4482, miR-4680, miR-548e, miR-6715a, miR-6715b, miR-4295, miR-4483, miR-2110, miR-3663, miR-4681, miR-4682, miR-3941, miR-4296, miR-4484, miR-4297, miR-378c, miR-202, miR-3944, miR-210, miR-4298, miR-675, miR-483, miR-4686, miR-4687, miR-302e, miR-5691, miR-4485, miR-4299, miR-6124, miR-6073, miR-3159, miR-4486, miR-4694, miR-610, miR-1343, miR-3973, miR-670, miR-129, miR-4688, miR-3160, miR-5582, miR-4487, miR-3161, miR-6128, miR-3162, miR-6503, miR-4488, miR-611, miR-6514, miR-1237, miR-192, miR-612, miR-4690, miR-4489, miR-3163, miR-4691, miR-3164, miR-3664, miR-3165, miR-139, miR-4692, miR-4696, miR-326, miR-708, miR-5579, miR-4300, miR-3166, miR-4490, miR-1261, miR-1304, miR-5481, miR-3920, miR-4693, miR-4491, miR-4301, miR-6716, miR-4492, miR-3656, miR-100, miR-4493, miR-3167, miR-6090, miR-4397, miR-3649, miR-141, miR-1244, miR-613, miR-614, miR-3974, miR-920, miR-4302, miR-4698, miR-130a, miR-548k, miR-120b, miR-34c, miR-34b, miR-125b, miR-let-7a, miR-200c, miR-4494, miR-6505, miR-1291, miR-4701, miR-1293, miR-615, miR-3198, miR-1228, miR-616, miR-6125, miR-6074, miR-6502, miR-1279, miR-3913, miR-1252, miR-617, miR-618, miR-4699, miR-5700, miR-492, miR-331, miR-3685, miR-1251, miR-4495, miR-4303, miR-1821, miR-3652, miR-4496, miR-619, miR-4497, miR-3657, miR-1302, miR-620, miR-4472, miR-1178, miR-4498, miR-4700, miR-4304, miR-3908, miR-5188, miR-4419, miR-3612, miR-4499, miR-2276, miR-4305, miR-320d, miR-196a, miR-148b, miR-26a, miR-let-7i, miR-548z, miR-548c, miR-135a, miR-621, miR-3168, miR-5006, miR-3613, miR-16, miR-15a, miR-5693, miR-4703, miR-759, miR-1297, miR-5007, miR-3169, miR-548x, miR-3665, miR-4500, miR-622, miR-17, miR-18a, miR-19a, miR-20a, miR-19b, miR-92a, miR-4501, miR-623, miR-4306, miR-2681, miR-4705, miR-1267, miR-4502, miR-6717, miR-4707, miR-208a, miR-208b, miR-4307, miR-3171, miR-624, miR-4503, miR-548y, miR-6076, miR-4504, miR-5580, miR-4308, miR-5586, miR-548h, miR-4706, miR-4708, miR-625, miR-5694, miR-4505, miR-4709, miR-1260a, miR-4506, miR-3173, miR-151b, miR-342, miR-345, miR-2392, miR-770, miR-493, miR-337, miR-665, miR-431, miR-433, miR-127, miR-432, miR-136, miR-370, miR-379, miR-411, miR-299, miR-380, miR-1197, miR-323a, miR-758, miR-329, miR-494, miR-1193, miR-543, miR-495, miR-376c, miR-376a, miR-654, miR-376b, miR-300, miR-1185, miR-381, miR-487b, miR-539, miR-889, miR-544a, miR-655, miR-487a, miR-382, miR-134, miR-688, miR-485, miR-323b, miR-154, miR-496, miR-377, miR-541, miR-409, miR-412, miR-369, miR-410, miR-656, miR-1247, miR-4309, miR-203a, miR-203b, miR-4710, miR-4539, miR-4507, miR-4537, miR-5195, miR-5701, miR-1268a, miR-4509, miR-4508, miR-4715, miR-211, miR-1233, miR-3942, miR-4510, miR-626, miR-4310, miR-627, miR-1282, miR-147b, miR-4716, miR-4712, miR-4713, miR-1266, miR-628, miR-2116, miR-6085, miR-190a, miR-4229, miR-1272, miR-4511, miR-4311, miR-4512, miR-629, miR-630, miR-4513, miR-631, miR-4313, miR-3713, miR-184, miR-5572, miR-549a, miR-4514, miR-4515, miR-1276, miR-1179, miR-7, miR-3529, miR-5094, miR-5009, miR-3174, miR-3175, miR-1469, miR-4714, miR-5587, miR-3176, miR-662, miR-3177, miR-1225, miR-6511b, miR-4516, miR-3180, miR-3677, miR-940, miR-4717, miR-3178, miR-193b, miR-365a, miR-3179, miR-3670, miR-6511a, miR-1972, miR-6506, miR-484, miR-548w, miR-4721, miR-4517, miR-4518, miR-4519, miR-762, miR-3181, miR-3935, miR-138, miR-328, miR-1538, miR-140, miR-4719, miR-4720, miR-3183, miR-22, miR-132, miR-212, miR-1253, miR-4520a, miR-4520b, miR-195, miR-497, miR-324, miR-3414, miR-4521, miR-3676, miR-744, miR-12969b, miR-4731, miR-1288, miR-33b, miR-1180, miR-4522, miR-4723, miR-451a, miR-451b, miR-144, miR-4732, miR-4532, miR-423, miR-3184, miR-4733, miR-4724, miR-193a, miR-4725, miR-362b, miR-632, miR-2909, miR-378j, miR-4734, miR-4726, miR-4727, miR-4728, miR-6510, miR-5010, miR-2117, miR-4315, miR-5089, miR-152, miR-1203, miR-10a, miR-3185, miR-6129, miR-6165, miR-3614, miR-142, miR-4736, miR-454, miR-301a, miR-6129, miR-6125, miR-3614, miR-142, miR-4736, miR-454, miR-301a, miR-4729, miR-21, miR-4737, miR-633, miR-3064, miR-5047, miR-6080, miR-634, miR-635, miR-4524b, miR-4524a, miR-3615, miR-3678, miR-4738, miR-636, miR-4316, miR-4739, miR-1268b, miR-4730, miR-657, miR-3065, miR-338, miR-1250, miR-4740, miR-3186, miR-4525, miR-6718, miR-3976, miR-4317, miR-5190, miR-4526, miR-133a, miR-1, miR-4741, miR-320f, miR-3975, miR-187, miR-3929, miR-4318, miR-924, miR-5583, miR-4319, miR-4527, miR-4743, miR-4744, miR-1539, miR-4320, miR-4528, miR-4529, miR-122, miR-3591, miR-5011, miR-4745, miR-3187, miR-1909, miR-1227, miR-4321, miR-637, miR-4746, miR-4747, miR-3940, miR-4999, miR-5589, miR-4322, miR-1238, miR-638, miR-4748, miR-199a, miR-5684, miR-5695, miR-6515, miR-24, miR-27a, miR-23a, miR-181c, miR-181d, miR-639, miR-1470, miR-3189, miR-640, miR-1270, miR-5196, miR-4530, miR-6714, miR-641, miR-4323, miR-4531, miR-6088, miR-330, miR-642a, miR-642b, miR-769, miR-320e, miR-3190, miR-4324, miR-150, miR-5088, miR-4749, miR-4750, miR-4751, miR-99b, miR-let-7e, miR-125a, miR-643, miR-512, miR-1323, miR-498, miR-515, miR-520e, miR-519e, miR-520f, miR-519c, miR-1283, miR-520a, miR-526b, miR-525, miR-523, miR-518f, miR-520b, miR-518b, miR-526a, miR-520c, miR-518c, miR-524, miR-517a, miR-519d, miR-520d, miR-516b, miR-526a, miR-518e, miR-518a, miR-518d, miR-516a, miR-517c, miR-520h, miR-521, miR-522, miR-519a, miR-527, miR-516a, miR-516b, miR-371a, miR-371b, miR-372, miR-935, miR-4752, miR-4754, miR-4261, miR-4429, miR-4262, miR-3681, miR-3125, miR-4757, miR-1301, miR-4263, miR-558, miR-4765, miR-4430, miR-559, miR-4431, miR-3682, miR-217, miR-216a, miR-216b, miR-4432, miR-5192, miR-4433, miR-4434, miR-4778, miR-3126, miR-5000, miR-4264, miR-6071, miR-4779, miR-4771, miR-4435, miR-4780, miR-4436a, miR-3127, miR-5696, miR-4772, miR-4265, miR-4436b, miR-4771, miR-4435, miR-4780, miR-4436a, miR-3127, miR-5696, miR-4772, miR-4265, miR-4436b, miR-4771, miR-4782, miR-4783, miR-4784, miR-663b, miR-3679, miR-5590, miR-128, miR-4773, miR-4785, miR-933, miR-10b, miR-1246, miR-4444, miR-3128, miR-6512, miR-1258, miR-561, miR-1245a, miR-1245b, miR-3606, miR-3129, miR-3130, miR-2355, miR-4775, miR-4776, miR-4438, miR-6513, miR-26b, miR-375, miR-3131, miR-153, miR-3132, miR-4268, miR-4439, miR-5702, miR-5703, miR-4777, miR-1471, miR-562, miR-5001, miR-4440, miR-4441, miR-4269, miR-2467, miR-4786, miR-149, miR-3138, miR-1292, miR-3192, miR-663a, miR-3193, miR-1825, miR-4755, miR-644a, miR-499a, miR-499b, miR-1289, miR-3646, miR-3617, miR-3616, miR-645, miR-3197, miR-4756, miR-4325, miR-4525, miR-296, miR-298, miR-646, miR-4533, miR-1257, miR-3195, miR-4758, miR-124, miR-3196, miR-4326, miR-941, miR-647, miR-3648, miR-3687, miR-999, miR-let-7c, miR-548x, miR-6130, miR-155, miR-4759, miR-4327, miR-6501, miR-802, miR-6508, miR-4760, miR-3197, miR-6070, miR-3198, miR-648, miR-4761, miR-185, miR-3618, miR-1306, miR-1286, miR-649, miR-301b, miR-130b, miR-650, miR-5571, miR-548j, miR-3199, miR-5739, miR-3653, miR-3200, miR-3928, miR-4764, miR-3909, miR-6069, miR-658, miR-659, miR-4534, miR-4766, miR-1281, miR-33a, miR-378i, miR-1249, miR-4762, miR-3619, miR-1184, miR-664b, miR-718, miR-3202, miR-767, miR-105, miR-452, miR-224, miR-4330, miR-2114, miR-514a, miR-510, miR-509, miR-514b, miR-507, miR-506, miR-513a, miR-513c, miR-891a, miR-891b, miR-892b, miR-888, miR-890, miR-892c, miR-504, miR-934, miR-424, miR-503, miR-542, miR-450a, miR-450b, miR-45b, miR-106a, miR-18b, miR-20b, miR-363, miR-3672, miR-766, miR-1277, miR-448, miR-1911, miR-1298, miR-1264, miR-1912, miR-764, miR-4329, miR-3978, miR-652, miR-6087, miR-518m, miR-361, miR-1321, miR-4328, miR-325, miR-384, miR-374a, miR-545, miR-374c, miR-374b, miR-421, miR-676, miR-223, miR-1468, miR-4536, miR-98, miR-502, miR-660, miR-500b, miR-501, miR-362, miR-500a, miR-188, miR-532, miR-4769, miR-222, miR-221, miR-1587, miR-3937, miR-3915, miR-4666b, miR-6134, miR-23c, miR-4768, miR-6086, miR-651, miR-4767, miR-4770, miR-6089, miR-3690, miR-602, miR-3621, miR-4479, miR-4292, miR-6722, miR-126, miR-4674, miR-4673, miR-3689a, miR-3689b, miR-3689c, miR-3689e, miR-3689d, miR-3689f, miR-4669, miR-2964a, miR-3154, miR-5683, miR-5689, miR-548a, miR-3143, miR-877, miR-4646, miR-1236, miR-6721, miR-219, miR-3934, miR-1275, miR-5690, miR-3925, miR-4462, miR-4647, miR-4642, miR-586, miR-206, miR-133b, miR-4282, miR-2113, miR-4643, miR-4464, miR-3674, miR-671, miR-3907, miR-4468, miR-490, miR-6509, miR-29a, miR-29b, miR-335, miR-3654, miR-6133, miR-183, miR-96, miR-182, miR-129, miR-593, miR-592, miR-6132, miR-106b, miR-93, miR-25, miR-591, miR-489, miR-653, miR-1286, miR-590, miR-1200, miR-550b, miR-55a, miR-196b, miR-148a, miR-589, miR-339, miR-1202, miR-30a, miR-587, miR-548b, miR-588, miR-199b, miR-181a, miR-3911, miR-601, miR-14a, miR-455, miR-32, miR-24, miR-23b, miR-27b, miR-let-7d, miR-let-7a, miR-let-7f, miR-4291, miR-4670, miR-4651, miR-4290, miR-204, miR-1299, miR-4477a, miR-4477b, miR-4540, miR-4475, miR-873, miR-876, miR-31, miR-491, miR-4474, miR-4473, miR-1234, miR-939, miR-661, miR-937, miR-151a, miR-30d, miR-30b, miR-5194, miR-661, miR-937, miR-4662, miR-151a, miR-3669, miR-3673, miR-, miR-1208, miR-1207, miR-1206, miR-1205, miR-1204, miR-4662a, miR-4662b, miR-4663, miR-3610, miR-2053, miR-5680, miR-4471, miR-875, miR-599, miR-3150a, miR-3150b, miR-4661, miR-3149, miR-2052, miR-5681a, miR-5681b, miR-4470, miR-4469, miR-486, miR-3148, miR-4288, miR-4287, miR-3622a, miR-3622b, miR-3926, miR-383, miR-598, miR-1322, miR-4286, miR-124, miR-597, miR-4660, miR-4659b, miR-596, miR-5707). It may also include any forms of microRNAs, preferably including a natural functional microRNA or an expression vector thereof, an artificially synthesized functional microRNA or an expression vector thereof, or a combination thereof.

The functional siRNA described in the present invention may include the siRNAs of various species, for instance, including functional siRNAs of animals, plants or microbes. It may also include any forms of siRNAs, preferably including a natural functional siRNA or an expression vector thereof, an artificially synthesized functional siRNA or an expression vector thereof, or a combination thereof. The artificially synthesized functional microRNA or siRNA used in the present invention can be obtained by synthesis according to the conventional methods in the art.

Use of Functional microRNAs and/or siRNAs Described in the Present Invention

The functional microRNAs and/or siRNAs described in the present invention can be used as active ingredients for preparing a composition to be applied to mammals (such as human), said composition forms cell microvesicles at a first site in the body of an animal and is delivered to a second site so as to improve a physiological state at the second site or treat a disease at the second site, in which the second site is different from the first site.

Among them, said disease includes those diseases specific to microRNAs and/or siRNAs, said diseases specific to microRNAs and/or siRNAs refer to those diseases which can be relieved or cured by said microRNAs and/or siRNAs, including (but not limited to) tumors, acute and chronic infectious diseases (such as virus influenza, virus hepatitis, acquired immunodeficiency syndrome, viral diseases such as SARS, bacterial diseases (for example tuberculosis, bacterial pneumonia), and other acute and chronic infectious diseases caused by various pathogenic microorganisms, and other acute and chronic diseases (such as respiratory system diseases, immune system diseases, blood and hematopoietic system diseases (such as circulatory diseases including cardiovascular and cerebrovascular diseases), metabolic diseases related to endocrine system, digestive system diseases, nervous system diseases, urinary system diseases, reproductive system diseases and motor system diseases).

Application Mode or Administration Mode Described in the Present Invention

The active ingredients described in the present invention can be administered through gastrointestinal, intranasal, tracheal, pulmonary, and intravenous or epidermal, intracutaneous, subcutaneous, intracardiac, intramuscular, intramedullary, intraperitoneal, extradural, intraoral, sublingual, ocular, endorectal, intravaginal, intraurethral, and intraaural routes of non-focus site and the like. The preferred application mode or administration mode includes oral, respiratory tract, injection, transdermal, mucosal, or cavity administration.

Among them, said oral administration mode includes swallowing and buccal dissolution and the like. Said respiratory tract administration mode is an inhalation mode, including ultrasonic atomizing inhalation, oxygen atomizing inhalation, hand-pressing atomizing inhalation and the like. Said injection administration mode includes intra-arterial injection, intramuscular injection, intracardiac injection, subcutaneous injection, intradermal injection and the like. Said transcutaneous administration or transdermal administration includes iontophoresis, electroporation transdermal method and the like. Said mucosal administration mode includes nasal mucosal administration, oral mucosal administration, ocular mucosal administration, rectal mucosal administration, uterine administration and vaginal mucosal administration and the like. Said cavity administration mode includes rectal administration, vaginal administration, urethral administration, nasal administration, ear canal administration and the like.

The First Site and the Second Site Described in the Present Invention

In the present invention, the second site described in the present invention is different from the first site described in the present invention.

The first site described in the present invention refers to various cells, tissues and/or organs in the body of animal which have the capability of absorbing a microRNA and/or siRNA and re-secreting same in an enclosed form of cell microvesicles. The examples are liver, lung, gastrointestinal tract, mammary gland, kidney, brain, spleen, lymph, thyroid, reproductive organ, blood cells, lymphocytes and the like.

The second site described in the present invention refers to another site where the cell microvesicles formed at the first site are delivered thereto and exert the function thereof; said second site includes cells, tissues and/or organs, for example brain, pineal body, pituitary gland, eye, ear, nose, mouth, pharynx, parotid, tonsil, esophagus, trachea, thyroid, thymus, mammary gland, lung, heart, stomach, intestines, appendix, liver, gallbladder, spleen, pancreas, kidney, ureter, bladder, urethra, uterus, ovary, fallopian tube, vagina, spermatic duct, prostate, penis, testis, anus, bones, muscles, connective tissues, nerve, lymph, colorectum, blood, bone marrow, skin and the like.

Cell Microvesicles

Cell microvesicles are membrane structure bodies having a diameter between 30-1000 nm secreted by cells in an organism in both normal and pathological state, which are natural small particles containing cellular contents and with membrane structure similar to cell membrane, including two types: exosome and shedding vesicle. Both in vivo and in vitro experiments showed that cell microvesicles can be secreted by a variety of cells including red blood cells, B cells, T cells, dendritic cells, mast cells, epithelial cells and tumor cells and the like. Cells allow specific bioactive molecules such as proteins and mRNA and the like to be enclosed in cell microvesicles, in which these bioactive molecules are delivered to corresponding recipient cells via cell microvesicles and regulate the biological function of the recipient cells; and this type of intercellular information transmission mediated by cell microvesicles plays a very important role in some physiological and pathological processes.

The cell microvesicles described in the present invention include various natural biological vesicles having bilayer lipid membrane and sizes of 10-500 nm which are secreted by cells, including exosome, shedding vesicles and the shedding vesicles secreted by various cells.

The "functional microRNA and/or siRNA enclosing cell microvesicles", "secretory microRNA and/or siRNA", "cell microvesicles-microRNA and/or siRNA complex" as used in the present invention can be used interchangeably.

The functional microRNA and/or siRNA enclosing cell microvesicles described in the present invention can be prepared according to the conventional method in the art, and preferably prepared according to the following steps: applying a functional microRNA and/or siRNA to a mammal (such as human) and allowing internalization of said functional microRNA and/or siRNA, thereby enclosing the internalized functional microRNA and/or siRNA at a certain site (such as the first site of the present invention) of said mammals to form cell microvesicles. Said cell microvesicles are releasable and can be delivered to another site (such as a focus site). For example, said cell microvesicles can enter the circulatory system of an animal and then enter a focus site.

The cell microvesicles described in the present invention enclose the functional microRNA and/or siRNA described in the present invention (that is, secretory microRNA and/or siRNA), and they are delivered to a focus site and exert effects of treating and preventing a disease of the focus site. The "secretory" refers to the microRNA or siRNA described above is processed into cell microvesicles after entering the body of an animal (such as human) and delivered (such as via blood circulation) to another site (i.e., a focus site).

The present invention provides a method for producing and detecting a secretory microRNA and/or siRNA, which comprises the steps of:

1. preparing a microRNA or siRNA;

the preparation mode of said microRNA or siRNA includes chemical synthesis of a microRNA mature sequence or a siRNA mature sequence, expression of the microRNA mature sequence or the siRNA mature sequence via a vector, or extraction of a natural microRNA or siRNA.

2. applying the microRNA or siRNA to an animal (such as human);

3. detecting the content of the secretory microRNA and/or siRNA in animal blood;

Said detecting applies methods comprising real-time fluorescent quantitative PCR method. Preferably, the particular method using said real-time fluorescent quantitative PCR method (Real-time PCR) for detecting the secretory microRNA and/or siRNA content includes the following steps: 1) extracting serum RNA; 2) performing reverse transcription (RT) on serum RNA, and then performing PCR amplification on its product cDNA. According to the CT value obtained from PCR reaction, the content of specific secretory microRNA and/or siRNA in serum which primarily participates in the reaction is deduced.

Pharmaceutical Composition

The active ingredient of the present invention refers to the functional microRNA and/or siRNA described in the present invention. Said microRNA and/or siRNA herein is enclosed at a first site of a mammal after being applied to said mammal so as to form cell microvesicles. Said cell microvesicles are releasable and can be delivered to a second site, and said second site is a focus site.

The pharmaceutical composition of the present invention comprises an active ingredient within the scope of a safe and effective amount and a pharmaceutically acceptable excipient or carrier. The "safe and effective amount" herein means that the amount of the active ingredient can obviously improve pathogenic condition without causing severe side effect. Generally, a pharmaceutical composition contains 1-2000 mg active ingredient/dose, and preferably contains 10-200 mg active ingredient/dose. More preferably, said "one dose" is an injection dose.

"Pharmaceutically acceptable carrier" means one or more compatible solid or liquid fillers or gel substances which are suitable for human use and have sufficient purity and low enough toxicity. "Compatibility" herein means that individual components can be incorporated with the active ingredient and incorporated with one another without obviously reducing the drug effect of the active ingredient. The examples of pharmaceutically acceptable carriers include cellulose and derivatives thereof (such as sodium carboxymethylcellulose, sodium ethyl cellulose and the like), gelatin, solid lubricant (such as stearic acid, magnesium stearate), calcium sulfate, a vegetable oil (such as soybean oil, olive oil and the like), polyols (such as propylene glycol, mannitol, sorbitol and the like), an emulsifying agent (such as Tween®), a wetting agent (such as sodium lauryl sulfate), a stabilizing agent, an antioxidant, a preservative, pyrogen-free water and the like.

The administration mode of the pharmaceutical composition described in the present invention is consistent with the application mode (or administration mode) described in the present invention.

The dosage form of the pharmaceutical composition described in the present invention is consistent with the administration mode, including for example (but not limited to), a tablet, a capsule, a powder, a pill, a granule, a syrup, a solution, a suspension liquid, an emulsion, a suspension, a spray, an aerosol, a powder spray, a volatile liquid, an injection, a powder for injection, a topical solution, a lotion, a pour agent, a liniment, a cataplasma, a medicinal paste, a rubber paste, an ointment, a plaster, a paste, an eye drop, a nasal drop, an ophthalmic ointment, a mouth wash, a sublingual tablet, or a suppository and the like.

Therapeutic Method

The present invention provides a therapeutic method comprising the step of applying at a first site (for example, a site far from a focus) the functional microRNA and/or siRNA described in the present invention to a subject (such as mammals, including human) in need of treatment, so as to treat a disease at a second site (i.e., the focus site) of said subject.

In another preferred example, said method comprises the step of applying at a first site the functional microRNA and/or siRNA described in the present invention to a subject in need of treatment, with said microRNA and/or siRNA being taken in and enclosed to form cell microvesicles which are released and delivered to a second site, so as to treat a disease at a second site of said subject; wherein, said second site is different from (preferably far from) the first site.

In another preferred example, said application mode (i.e., administration mode) preferably includes oral, respiratory tract, injection, transdermal, mucosal, and cavity administration, etc. The details thereof are as described above. Said first site or second site is as described above.

The present invention also provides a therapeutic method which comprises the step of applying the pharmaceutical composition described in the present invention to a subject in need of treatment so as to treat a disease of said subject.

The present invention provides a more preferred therapeutic method, which particularly comprises the steps of (1) determining the microRNA and/or siRNA capable of exerting therapeutic effects on a disease according to the type of the disease; (2) preparing the corresponding microRNA or siRNA; (3) injecting the microRNA or siRNA to a human body; (4) detecting the content of the secretory microRNA or siRNA in serum in vivo; (5) detecting the content of the microRNA or siRNA in a target cell; (6) detecting the changing of the function of the target cell; and (7) detecting the therapeutic effects on the disease.

The Advantages of Cell Microvesicle-Mediated microRNA Delivery as a Novel Administration Mode for Treating Diseases As cell microvesicles are natural particles containing cellular contents, secreted by cells, and enclosed by a membrane structure similar to cell membrane, they can very easily enter cells and have no toxic or side effects. Therefore, cell microvesicles are highly efficient pharmaceutical carriers. As cell microvesicles can be secreted by cells constantly, they are relatively easy to get at low costs. Modified microvesicles can also specifically target recipient cells such as tumor cells, so as to treat diseases.

The main advantages of the present invention are that:

1. a method for ex situ treatment of a disease is provided, said method comprises applying a functional microRNA/siRNA at a certain site far from a focus site (such as common bile duct) of a patient to form cell microvesicles, i.e., "cell microvesicle-functional microRNA/siRNA" complexes, which are delivered (for instance, by means of entering circulatory system) to a focus site (such as lymphocytes and the like), thereby realizing the effect of treating a disease of the focus site.

2. cell microvesicles as a natural biocompatible material, which act as a carrier to mediate the delivery of an exogenous microRNA and siRNA, will facilitate the treatment of diseases via systematic administration using the microRNA and siRNA as the disease-resistant drugs. It will have tremendous application prospect and market value to develop cell microvesicle-mediated exogenous microRNA as a drug for treating diseases.

The present invention is further illustrated in connection with particular embodiments as follows. It should be understood that these embodiments are merely illustrative of the invention and are not intended to limit the scope of the present invention. In the case of specific conditions for the experimental method being not specified in the following examples, generally conventional conditions are followed, such as the conditions described in Sambrook et al., *Molecular Cloning: A Laboratory Manual* (New York: Cold Spring Harbor Laboratory Press, 1989), or the conditions recommended by the manufacturer are followed. All percentages and parts are by weight unless otherwise indicated.

Example 1 Intravenously-Injected Artificially-Synthesized siRNA can Enter Liver Cells and Lymphocytes In this example, the artificially-synthesized siRNA is injected into the body of mice via tail vein injection. The siRNA in the body of mice is reabsorbed by liver cells and is again secreted via cell microvesicles into blood to form "cell microvesicle-siRNA complex". The lymphocytes in the circulatory system then internalize the "cell microvesicle-siRNA complex", and the siRNA in the complex enters the lymphocytes and plays a corresponding role.

The Main Experimental Materials:

Balbc male mice (18-22 g), pentobarbital sodium, syringe, artificially synthesized siRNA 092-3 and NC (Shanghai GenePharma Co., Ltd), Lymphocyte Separation Medium (Tianjin Haoyang Biological Products Technology Co., Ltd.), TaqMan probes (miR-U6 and 092-3) and reagents for real-time fluorescent quantitative PCR (Real-Time quantitative PCR) (Takara BIO Inc.).

Experimental Method and Steps:

1. Animal experiment: male Balbc mice (Model Animal Research Centre of Nanjing University) are fed for 3 days, followed by enrolling the mice with normal food intake, drinking, and activities into the experiment. The mice after being randomly divided into groups are injected via tail veins with physiological saline (Normal group), negative control siRNA (NC group) and 092-3 siRNA (092-3 group) respectively, the mice are sacrificed at 6 h, 12 h, 18 h and 24 h, and blood and liver tissues are collected.

2. Separation of lymphocytes: 1 ml fresh anticoagulated blood and PBS are mixed in 1:1, followed by adding same onto the liquid level of 2 ml lymphocyte isolation liquid, centrifuging at a speed of 2000 rpm for 15 min to allow the contents in the centrifuge tube to be layered into four layers from top to bottom, collecting the lymphocytes of the second ring-shaped milk white layer and placing same into a tube containing 4-5 ml PBS, mixing uniformly and thoroughly, and centrifuging at a speed of 2000 rpm for 20 min to obtain the lymphocytes as pellets.

3. Detection of 092-3 siRNA Level in Liver Tissues and Lymphocytes Using Real-Time Quantitative PCR:

(1) RNA is extracted from lymph tissue and liver tissue using Trizol reagent (Invitrogen Co., Ltd.);

(2) cDNA is obtained via RNA reverse transcription reaction, in which the reaction system is: 2 μl RNA of lymphocytes or liver tissue, 2 μl 5×AMV buffer, 1 μl 10 mM mixture of various dNTPs (Takara BIO Inc.), 0.5 μl AMV (Takara BIO Inc.) and 1 μl miR-U6 or 092-3 reverse transcription primer (USA Applied Biosystem Inc.), added up to volume of 10 μl using 3.5 μl DEPC water.

(3) Real-Time quantitative PCR is performed, in which the reaction system and reaction procedure are as shown in Table 1 as follows:

TABLE 1

| PCR water | 14.77 μl |
|---|---|
| 10 × buffer | 2 μl |
| MgCl$_2$ | 1.2 μl |
| dNTP | 0.4 μl |
| Taq enzyme | 0.3 μl |
| TaqMan probe | 0.33 μl |
| cDNA | 1 μl |

PCR reaction is performed under the following conditions: at 95° C. for 5 min, at 95° C. for 15 s, at 60° C. for 1 min, 40 cycles.

(4) The detection results are analyzed

Figure 1A:
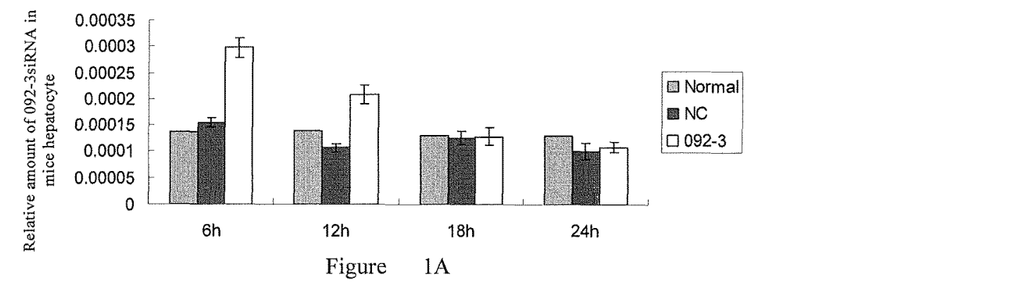
FIG. 1A displays the change in content of 092-3siRNA in liver cells of mice after intravenously injecting artificially synthesized siRNA.

The results show that the content of the exogenous siRNA in the liver of mice rises significantly 6 hours after tail vein injection of artificially synthesized siRNA 092-3 (Shanghai GenePharma Co., Ltd), and it is still higher than normal level after 12 hours, but slightly lower than that after 6 hours. Afterwards, the content restores to normal condition after 18 hours, with the results being shown in FIG. 1A. In this figure, Normal group represents the group of tail vein injection of physiological saline, NC group represents tail vein injection of artificially synthesized negative control siRNA, and 092-3 group represents tail vein injection of artificially synthesized siRNA.

Figure 1B:
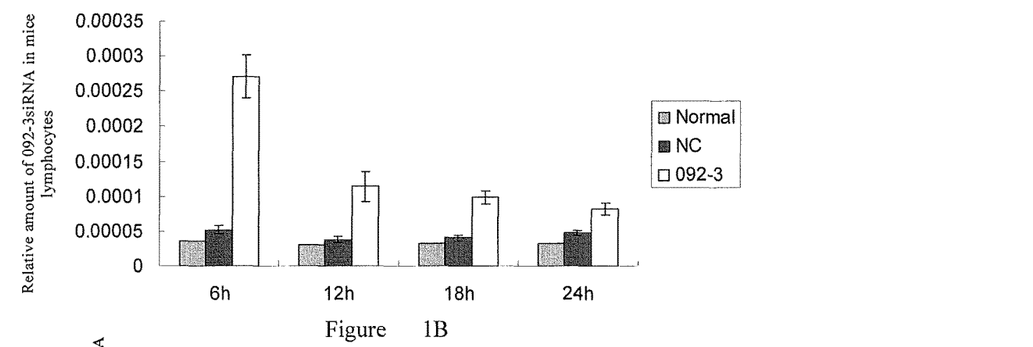
FIG. 1B displays the change in content of 092-3siRNA in lymphocytes of mice after intravenously injecting artificially synthesized siRNA.

Likewise, the highly expressed exogenous siRNA in the lymphocytes of mice is detected 6 hours after tail vein injection of artificially synthesized 092-3, the high concentration thereof continues to 18 hours after injection, and it is gradually restored to normal 24 hours after injection, with the results being shown in FIG. 1B.

It can be seen from the above-mentioned results that said exogenous siRNA can be absorbed by relevant tissue such as liver through blood circulation after intravenous injection of artificially synthesized siRNA.

Said exogenous siRNA also enters lymphocytes. However, there may be two reasons for said exogenous siRNA entering lymphocytes: (1) liver, as a generator, can process exogenous siRNA into siRNA enclosed by cell microvesicles, or so-called "cell microvesicles-siRNA complex", and said secretory siRNA then enters circulatory system and is absorbed by the lymphocytes in the circulatory system, thereby entering therein. (2) the lymphocytes may directly phagocytose free siRNA in the blood after intravenous injection, thus resulting in raised content of siRNA in lymphocytes.

Therefore, in order to exclude the second possibility, the inventors carry out the following experiment (see example 2).

Example 2 Artificially Synthesized microRNA Injected Via Common Bile Duct of Mice can Enter Liver and T Cells In this example, artificially synthesized microRNA HA2-1 is injected to the common bile duct of mice, and the results show that exogenous microRNA can also enter liver cells and lymphocytes under this injection mode.

The Main Experimental Materials:

Balbc male mice (18-22 g), pentobarbital sodium, artificially synthesized microRNA (HA2-1), surgical instruments, intravenous injection needles, syringes, surgical sutures, Lymphocyte Separation Medium (Tianjin Haoyang Biological Products Technology Co., Ltd.) and reagents for real-time fluorescent quantitative PCR (Takara BIO Inc.).

Experimental Method and Steps:

1. Animal Experiments:

(1) mice are narcotized with pentobarbital sodium in a dose of 40 mg/kg body weight;

(2) the narcotized mice are fixed on a test bench and cut under the abdominal diaphragm (at the site of liver) a wound of about 1-2 cm, and the common bile duct is seen;

(3) artificially synthesized microRNA is injected into the common bile duct with the direction of the needle being directed to the liver and the injection amount being 200 microliters, and the injection is proved to be successful when the site of liver adjacent to the common bile duct having slightly turned white [is observed];

(4) the wound of mice is sutured and the mice are placed at a warm place and sacrificed after 16 hours, and blood and liver tissues are collected.

2. The subsequent experimental steps for lymphocyte separation and content detect of HA2-1 in liver tissues and lymphocytes using Real-Time quantitative PCR are the same as that of example 1.

Figure 2A:
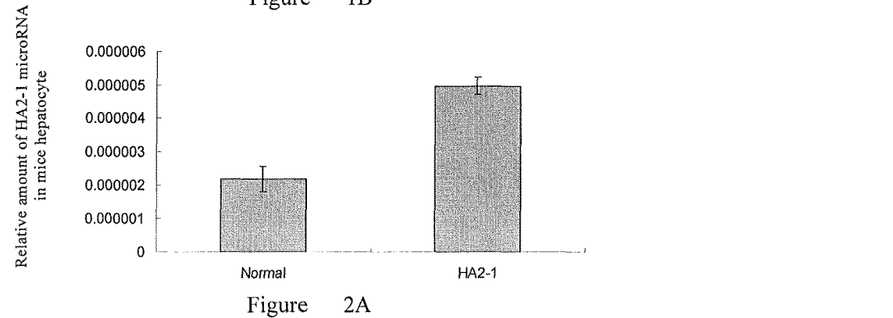
FIG. 2A displays the change in content of HA2-1microRNA in liver cells of mice after common bile duct injection of artificially synthesized microRNA.
Figure 2B:
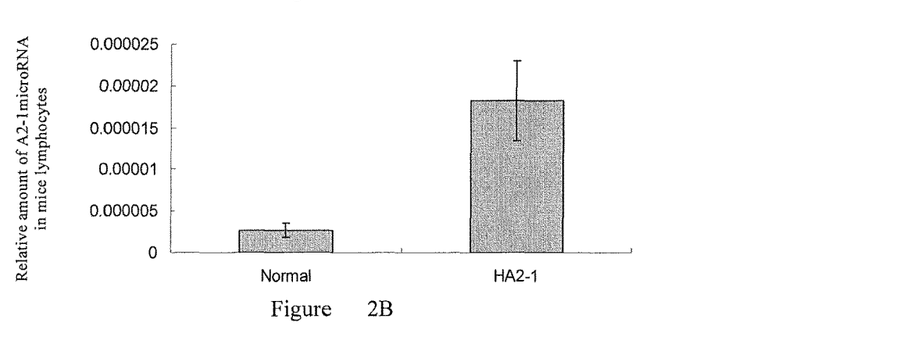
FIG. 2B displays the change in content of HA2-1microRNA in lymphocytes of mice after common bile duct injection of artificially synthesized microRNA.

The results are shown in FIG. 2A and FIG. 2B, the expression of exogenous microRNA in liver and lymphocytes of mice also rises significantly 16 hours after injecting artificially synthesized microRNA via the common bile duct into mice. In this figure, the Normal group represents the group of tail vein injection of physiological saline injection, and the HA2-1 group represents tail vein injection of artificially synthesized microRNA.

In this example, lymphocytes do not directly contact with the free microRNA injected into the body of mice, therefore, this result excludes the possibility raised in example 1 that lymphocytes may directly phagocytose free microRNA in the blood after intravenous injection, resulting in the elevation of the content of microRNA in lymphocytes.

It is further demonstrated that the mode of the exogenous microRNA entering lymphocytes is: the microRNA injected via common bile duct enters liver→the microRNA is secreted by liver cells to the circulatory system in the form of "cell microvesicles-microRNA complex"→the "cell microvesicles-microRNA complex" in the circulatory system is captured by the lymphocytes in blood and thus enters the lymphocytes.

The inventors also carry out experiment of mice common bile duct injection of artificially synthesized siRNA, and the results show that the artificially synthesized siRNA also enters liver cells and lymphocytes after common bile duct injection, which demonstrate that the mode of exogenous siRNA entering lymphocytes is the same as above: the siRNA enters liver via common bile duct injection→the siRNA is secreted by liver cells into the circulatory system in the form of cell microvesicles→the cell microvesicles in the circulatory system are captured by the lymphocytes in blood and thus enter the lymphocytes.

Example 3 Intravenously Injected microRNA Expression Plasmids can Enter Liver and T Cells The Main Experimental Materials:

Balbc male mice (18-22 g), pentobarbital sodium, syringe, artificially constructed plasmid (pAd-miR-145) and adenovirus (Ad-miR-145) (our laboratory) overexpressing miR-145, Lymphocyte Separation Medium (Tianjin Haoyang Biological Products Technology Co., Ltd.), TaqMan probes (miR-U6 and miR-145) and reagents for Real-Time quantitative PCR (Takara BIO Inc.).

Experimental Method and Steps:

1. Construction of Recombinant Adenovirus Overexpressing miR-145 (Ad-miR-145)

(1) construction of recombinant plasmid pCMV-miR-145

The genome of mice is extracted, the pre-miR-145 sequence of miR-145 is cloned, followed by digesting same with an enzyme, ligating the cloned fragment of interest via an enzyme to pAdTrack-CMV vector digested with PacI, then identifying same by sequencing, and naming the correct clone as pCMV-miR-145.

(2) construction of recombinant adenovirus shuttle plasmid pAd-miR-145

The pCMV-miR-145 plasmid constructed in the previous step is digested with PmeI and linearized, followed by electroporation cotransformation into BJ5183 together with adenovirus framework plasmid pAdEasy-1. The correct clone after sequencing identification is named as pAd-miR-145 (miR-145 plasmid), while empty vector adenovirus pAd-control (control plasmid) is prepared as a negative control.

(3) acquisition, amplification and purification of recombinant adenoviruses Ad-control and Ad-miR-145

The above-mentioned recombinant adenovirus plasmids pAd-miR-145 and pAd-control are extracted and transfected to HEK 293T cells, of which 70% have been adhered to wall, and the formation of plaque and the expression of green fluorescent protein gene carried by the virus are observed under a fluorescence microscope. The diseased cells are collected 12-14 days after transfection, lysing the cells by repeated freezing and thawing at −80° C. and 37° C. for 3-4 times, followed by centrifuging under 100,000 g at 4° C. for 10 min, collecting supernatant containing viruses, again infecting HEK 293T cells using the collected supernatant, amplifying adenovirus in large scale and carrying out identification. Afterwards, the viruses are purified according to the operating instructions of a virus purification kit, the virus titers of Ad-miR-145 recombinant virus and Ad-control empty vector virus are determined using plaque assay, and finally the prepared high titer Ad-miR-145 recombinant virus and Ad-control empty vector virus are stored at −80° C. for later use.

2. animal experiment: the same as example 1, with the differences that the materials for tail vein injection are pAd-miR-145, pAd-control, Ad-miR-145, and Ad-control, respectively.

3. The subsequent experimental steps for lymphocyte separation and content test of miR-145 in liver tissues and lymphocytes using Real-Time quantitative PCR are the same as that of example 1.

Figure 3A:
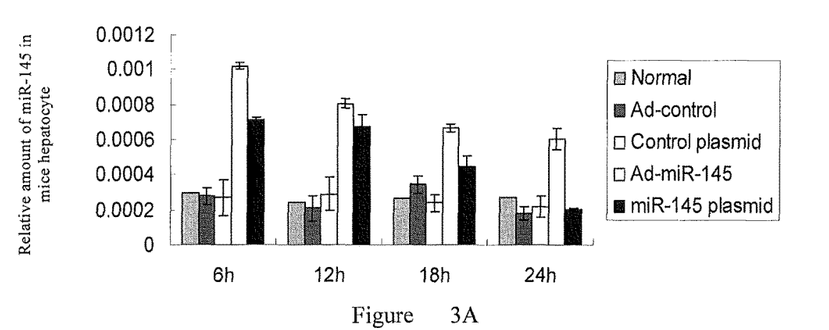
FIG. 3A displays the change in content of miR-145 in liver cells of mice after intravenously injecting microRNA expression plasmid or microRNA recombinant adenovirus.
Figure 3B:
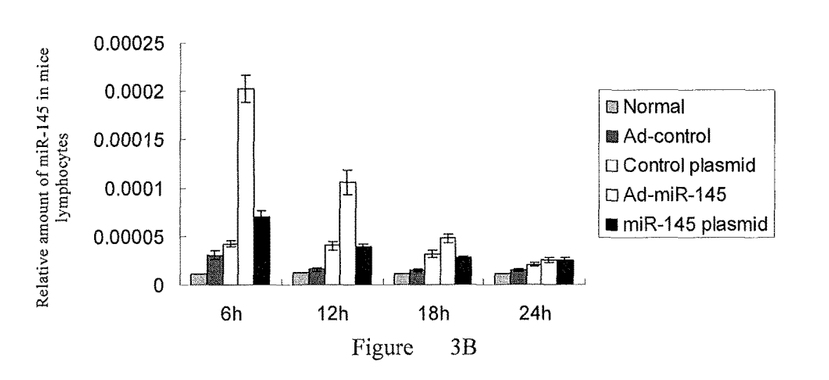
FIG. 3B displays the change in content of miR-145 in lymphocytes of mice after intravenously injecting microRNA expression plasmid or microRNA recombinant adenovirus.

The results are shown in FIG. 3A and FIG. 3B, in which,

Normal group represents tail vein injection of physiological saline;

The control plasmid group represents tail vein injection of recombinant plasmid negative control;

The Ad-control group represents tail vein injection of recombinant adenovirus negative control;

The miR-145 plasmid group (that is pAd-miR-145 group) represents tail vein injection of miR-145 overexpressing recombinant plasmid;

The Ad-miR-145 group represents tail vein injection of miR-145 overexpressing recombinant adenovirus;

The results show that the content of the miR-145 in the liver of mice rise significantly 6 hours after injecting the plasmid and the adenovirus overexpressing miR-145 via tail vein into the body of mice, and it is still higher than normal level after 12 hours, but slightly lower than that after 6 hours. In the subsequent 18 hours, the expression of miR-145 in liver tissues of mice of the group injected with plasmids overexpressing miR-145 decreases rapidly, and restores to the normal condition until 24 hours; however, the miR-145 level in the liver tissues of mice injected with adenovirus overexpressing miR-145 is still higher than that of the normal group, with the results shown in FIG. 3A.

Highly expressed miR-145 is also detected in the lymphocytes of mice 6 hours after tail vein injection of plasmids and adenovirus overexpressing miR-145. However, for the group injected with adenoviruses overexpressing miR-145, its high concentration continues to 18 hours after injection, while for the group injected with plasmids overexpressing miR-145, its high concentration only maintains 6 hours after injection and restores to the normal condition 12 hours after injection, with the results as shown in FIG. 3B.

This example demonstrates that the expressions of miR-145 in both liver and lymphocytes of mice are significantly raised through injecting plasmids and adenoviruses overexpressing miR-145 into the body of mice via tail vein, which indicates that exogenously expressed miRNA can enter a first site and said second site through blood circulation.

Example 4 The Changes in Physiological/Pathologic Conditions after Functional microRNA Entering the Body of Animals This example demonstrates that the plasmids expressing functional microRNAs and siRNAs enter the body of an animal and are delivered to a second site (a focus), and regulate the physiological/pathologic conditions of the animal so as to realize the effect of treating a diseases of the focus site.

The main experimental materials: Balbc mice (18-22 g) (Nanjing University Animal Model Centre), colorectal cancer model mice (constructed by our laboratory), pentobarbital sodium, artificially constructed plasmid overexpressing miR-145 (pAd-miR-145) and adenovirus overexpressing miR-145 (Ad-miR-145) and plasmid overexpressing miR-143 (pAd-miR-143) and adenovirus overexpressing miR-143 (Ad-miR-143) (constructed by our laboratory), surgical instruments, intravenous injection needles, syringes, surgical sutures (Tianjin Haoyang Biological Products Technology Co., Ltd.) and reagents for Real-Time quantitative PCR (Takara BIO Inc.).

In this example, Normal group represents tail vein injection of physiological saline;

The control plasmid group represents tail vein injection of recombinant plasmid negative control;

The Ad-control group represents tail vein injection of recombinant adenovirus negative control;

The pAd-miR-145 group represents tail vein injection of miR-145 overexpressing recombinant plasmid;

The Ad-miR-145 group represents tail vein injection of miR-145 overexpressing recombinant adenovirus;

The pAd-miR-143 group represents tail vein injection of miR-143 overexpressing recombinant plasmid;

The Ad-miR-143 group represents tail vein injection of miR-143 overexpressing recombinant adenovirus;

4.1. Construction of Recombinant Plasmid (pAd-miR-145), Recombinant Adenovirus (Ad-miR-145) Overexpressing miR-145 and Recombinant Plasmid (pAd-miR-143) and Recombinant Adenovirus (Ad-miR-143) Overexpressing miR-143

The particular operating steps for the construction of recombinant plasmids pAd-miR-145 and pAd-miR-143 as well as the acquisition, amplification, and purification of recombinant adenoviruses Ad-miR-145 and Ad-miR-143 are as described in example 3.

4.2. Preparation of Colorectal Cancer Model Mice (1) Colorectal cancer cell line LoVo is cultured under SPF grade sterile experimental environment;

(2) The successfully cultured colorectal cancer LoVo cells are digested with trypsin under SPF grade sterile experimental environment, and prepared into a cell suspension with a cell concentration of $2 \times 10^6$ cells/mL;

(3) 0.5 mL of cell suspension is taken and subcutaneously inoculated using a sterile needle tubing at the right back of naked mice, and the inoculation is done within 30 minutes;

(4) The tumor inoculation conditions are periodically observed, and it is indicated that animal tumor modelling is successful when all of the subcutaneous tumor masses had grown to diameters of 0.6-0.8 cm after 9 days.

4.3. Changes in Functional microRNA and Target Genes in the Body of Colorectal Cancer Model Mice after Intravenously Injecting Functional microRNA 4.3.1 Animal Grouping Colorectal cancer model mice are fed for 3 days after successful modelling, and the mice having normal food intake, drinking, and activities are enrolled into the experiment after the 3 days. The mice after being randomly divided into groups are injected via tail veins with physiological saline (Normal group), plasmid negative control (pAd-control group), adenovirus negative control (Ad-control group), pAd-miR-145 (pAd-miR-145 group), Ad-miR-145 (Ad-miR-145 group), pAd-miR-143 (pAd-miR-143 group) and Ad-miR-143 (Ad-miR-143 group) respectively, the mice are sacrificed after 6 hours, and blood, liver, and colorectum are collected.

4.3.2 Lymphocyte Separation

The particular operating steps for lymphocyte separation are as described in example 1.

4.3.3. Change in Functional microRNA in the Body of Colorectal Cancer Model Mice after Intravenously Injecting Functional microRNA The contents of miR-145 and miR-143 in liver tissue, lymphocytes, and colorectal tissues are detected using Real-time PCR, and the experimental steps thereof are as described in example 1. The particular experiments are shown in FIG. 4 and FIG. 5.

Figure 4A:
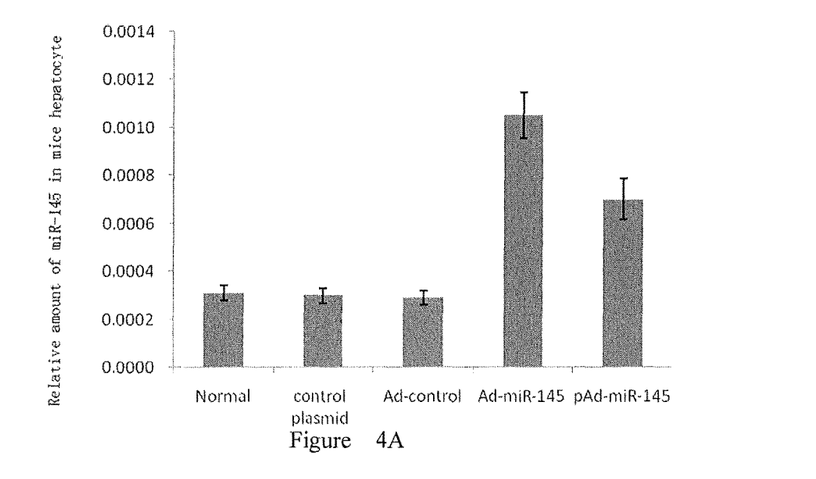
FIG. 4A displays the change in content of miR-145 in liver cells of mice after intravenously injecting microRNA expression plasmid or microRNA recombinant adenovirus.
Figure 5A:
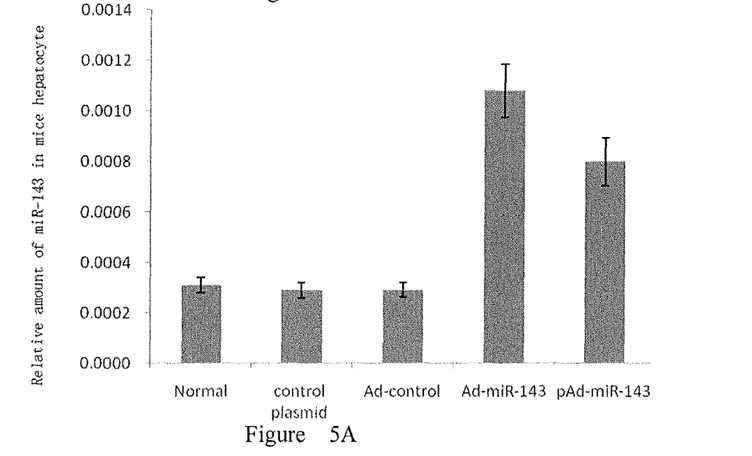
FIG. 5A displays the change in content of miR-143 in liver cells of mice after intravenously injecting microRNA expression plasmid or microRNA recombinant adenovirus.
Figure 5B:
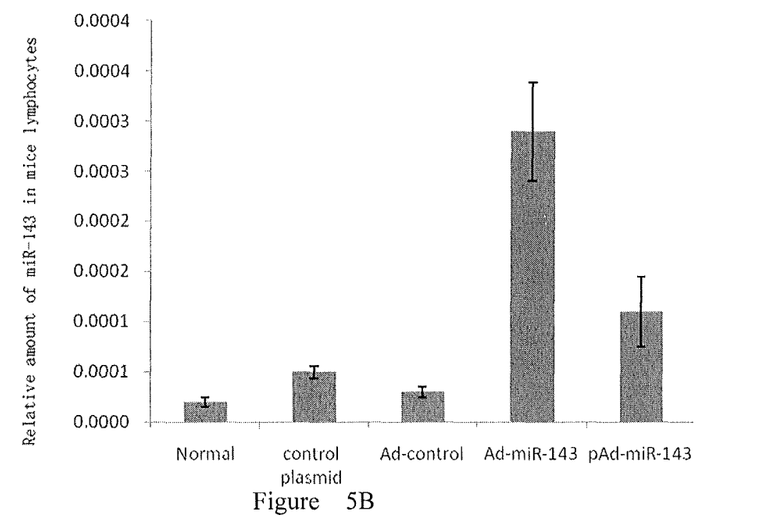
FIG. 5B displays the change in content of miR-143 in lymphocytes of mice after intravenously injecting microRNA expression plasmid or microRNA recombinant adenovirus.
Figure 5C:
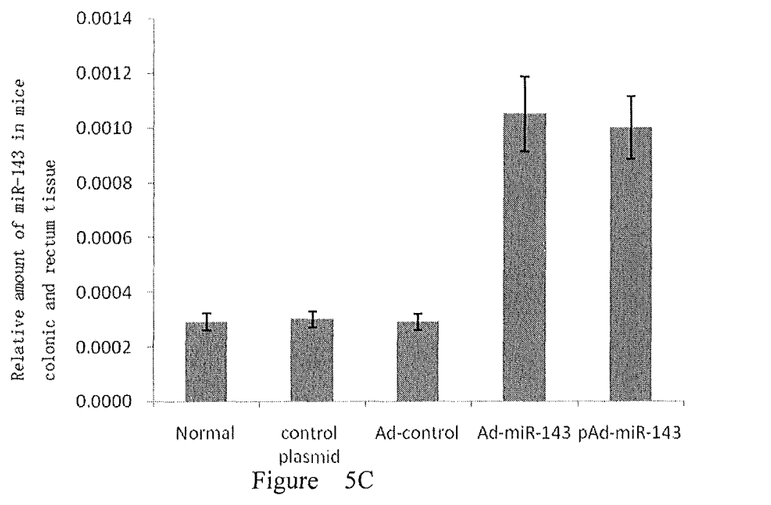
FIG. 5C displays the change in content of miR-143 in colorectal cells of mice after intravenously injecting microRNA expression plasmid or microRNA recombinant adenovirus.

FIG. 4A shows that miR-145 is overexpressed in the body of colorectal cancer model mice via tail vein injection, and after 6 hours, the level of miR-145 in liver tissues of colorectal cancer model mice is significantly higher than that of the normal group, which is increased by 3-4 times.

Figure 4B:
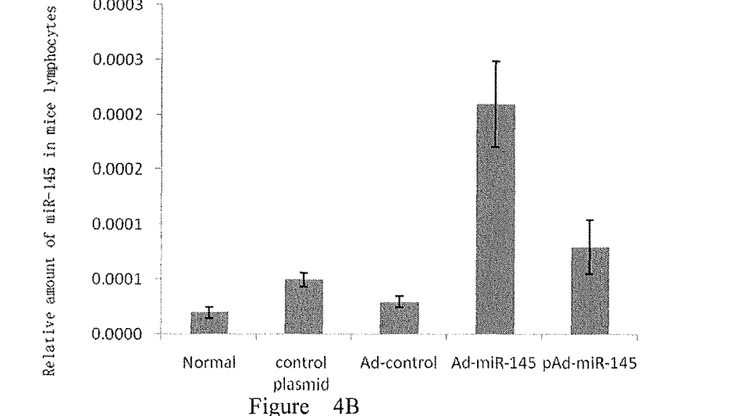
FIG. 4B displays the change in content of miR-145 in lymphocytes of mice after intravenously injecting microRNA expression plasmid or microRNA recombinant adenovirus.

FIG. 4B shows that miR-145 is overexpressed in the body of colorectal cancer model mice after tail vein injection, and after 6 hours, the level of miR-145 in lymphocytes of colorectal cancer model mice is significantly higher than that of the normal group, which is increased by about 7 times.

Figure 4C:
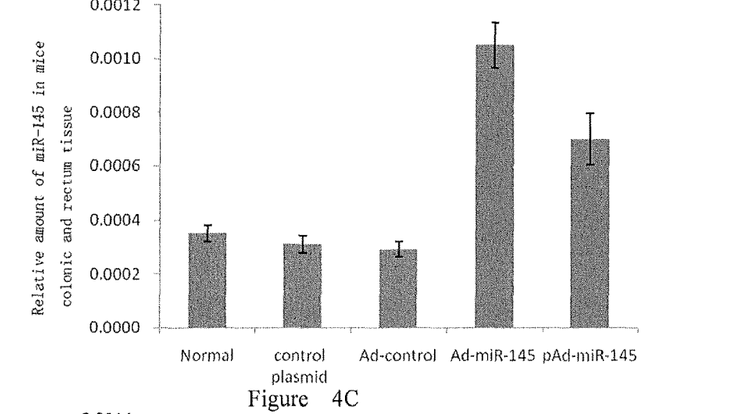
FIG. 4C displays the change in content of miR-145 in colorectal cells of mice after intravenously injecting microRNA expression plasmid or microRNA recombinant adenovirus.

FIG. 4C shows that miR-145 is overexpressed in the body of colorectal cancer model mice after tail vein injection, and after 6 hours, the level of miR-145 in colorectal tissues of colorectal cancer model mice is significantly higher than that of the normal group, which is increased by 3-4 times.

FIG. 5A shows that miR-143 is overexpressed in the body of colorectal cancer model mice after tail vein injection, and after 6 hours, the level of miR-143 in liver tissues of colorectal cancer model mice is significantly higher than that of the normal group, which is increased by 3-4 times.

FIG. 5B shows that miR-143 is overexpressed in the body of colorectal cancer model mice after tail vein injection, and after 6 hours, the level of miR-143 in lymphocytes of colorectal cancer model mice is significantly higher than that of the normal group, which is increased by about 9 times.

FIG. 5C shows that miR-143 is overexpressed in the body of colorectal cancer model mice after tail vein injection, and after 6 hours, the level of miR-143 in colorectal tissues of colorectal cancer model mice is significantly higher than that of the normal group, which is increased by 3-4 times.

The expressions of both miR-145 and miR-143 in the liver, lymphocytes, and colorectal tissues of the mice are raised significantly through tail vein injection of overexpressed pAd-miR-145, pAd-miR-143, Ad-miR-145, and pAd-miR-143 into the body of colorectal cancer model mice, which demonstrates that said functional microRNA is absorbed by the tissues such as a first site (e.g., liver) via blood circulation and further enclosed in MV by the first site, and is secreted out and enters other cells or tissues including lymphocytes and colorectum through blood circulation. Said administration mode can realize stable existence and therefore efficacy on the focus of the drugs.

4.3.4 Change in Target Genes of Colorectal Cancer Model Mice In Vivo after Intravenously Injecting Functional microRNA The expression levels of the target gene MYC of miR-145 and the target gene K-ras of miR-143 in colorectal tissues are detected using Real-time PCR, and the experimental steps thereof are as described in example 1. The detailed results are shown in FIG. 6 and FIG. 7.

Figure 6A:
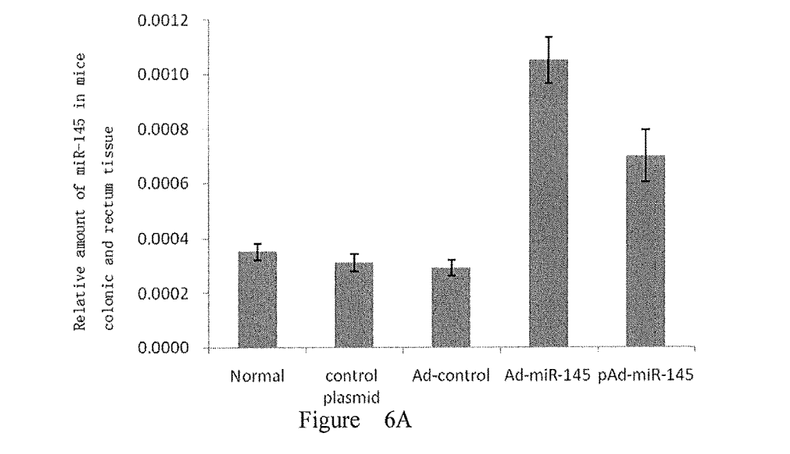
FIG. 6A displays the change in content of miR-145 in colorectal cells of mice after intravenously injecting microRNA expression plasmid or microRNA recombinant adenovirus.

It is showed in FIG. 6A that miR-145 is overexpressed in the body of colorectal cancer model mice after tail vein injection, and after 6 hours, the expression level of miR-145 in colorectal tissues is significantly increased as compared with the control group.

Figure 6B:
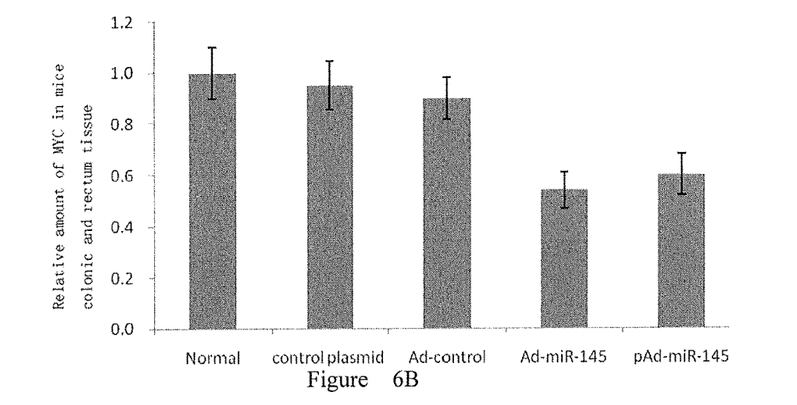
FIG. 6B displays the change in expression amount of miR-145 target gene MYC in colorectal cells of mice after intravenously injecting microRNA expression plasmid or microRNA recombinant adenovirus.

It is showed in FIG. 6B that miR-145 is overexpressed in the body of colorectal cancer model mice after tail vein injection, and after 6 hours, the expression of the target gene MYC of miR-145 in colorectal tissues is significantly decreased as compared with the control group, and the result demonstrates that the expressed miR-145 enters the body of colorectal cancer model mice to reduce the expression of the target gene, thereby can achieve the objects of inhibiting the growth of tumor focus and improving the pathological conditions of the focus.

Figure 7A:
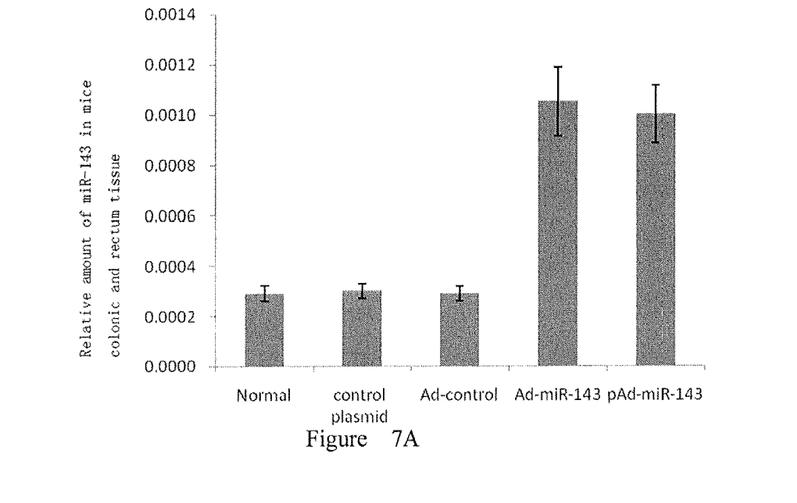
FIG. 7A displays the change in content of miR-143 in colorectal cells of mice after intravenously injecting microRNA expression plasmid or microRNA recombinant adenovirus.
Figure 7B:
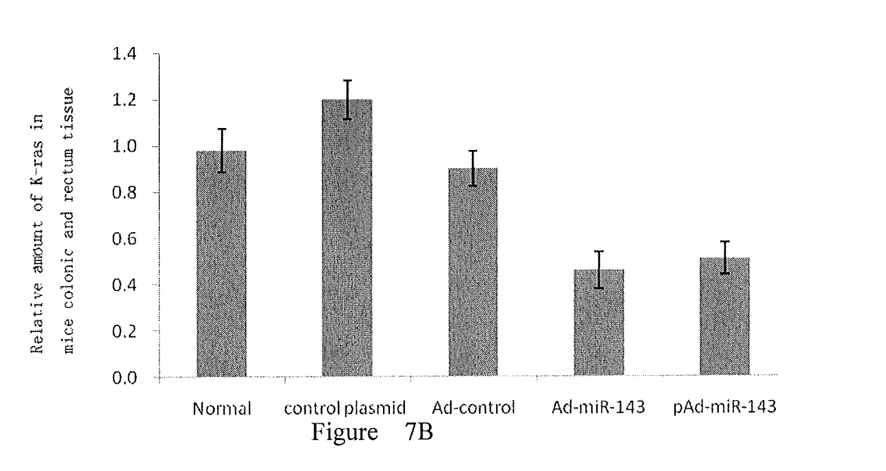
FIG. 7B displays the change in expression amount of miR-143 target gene K-ras in colorectal cells of mice after intravenously injecting microRNA expression plasmid or microRNA recombinant adenovirus.

It is showed in FIG. 7A that miR-143 is overexpressed in the body of colorectal cancer model mice after tail vein injection, and after 6 hours, the expression level of miR-143 in colorectal tissues is significantly increased as compared with the control group.

It is showed in FIG. 7B that miR-143 is overexpressed in the body of colorectal cancer model mice after tail vein injection, and after 6 hours, the expression of the target gene K-ras of miR-143 in colorectal tissues is significantly decreased as compared with the control group, and the result demonstrates that the overexpressed miR-143 enters the body of colorectal cancer model mice to reduce the expression of the target gene, thereby can achieve the objects of inhibiting the growth of tumor focus and improving the pathological conditions of the focus.

4.4. Change in Tumor in the Body of Colorectal Cancer Model Mice after Intravenously Injecting Functional microRNA 4.4.1 Animal Grouping Colorectal cancer model mice are fed for 3 days after successful modelling, and the mice having normal food intake, drinking, and activities are enrolled into the experiment after the 3 days. The mice after being randomly divided into groups are injected via tail veins with physiological saline (Normal group), plasmid negative control (pAd-control group), adenovirus negative control (Ad-control group), pAd-miR-145 (pAd-miR-145 group), Ad-miR-145 (Ad-miR-145 group), pAd-miR-143 (pAd-miR-143 group) and Ad-miR-143 (Ad-miR-143 group) respectively for successive 14 days. The mice are sacrificed on the next day after the last injection and dissected.

4.4.2 Observation of Indexes and Results

The maximum diameter a and the transverse diameter b of the tumors in vivo and the naked tumors obtained after dissecting and stripping are measured using a vernier during the course of the experiment and after the animals are sacrificed, and the volumes of the tumors in vivo and the naked tumors are calculated according to the formula $V=\pi/6 \times a \times b^2$. The growth rates of the living tumors are compared using $V_{GR}(V_{GR}(V_1-V_0)/t_{course\ of\ disease}, mm^3/d)$, in which $V_1$ is the volume size of the tumor in vivo after injection, $V_0$ is the tumor size of the tumor in vivo on the day of successful modelling; and the tumor inhibition rate is calculated: $P_{tumor\ inhibition}=[1-(m_{injection\ group}/m_{control\ group})] \times 100\%$; in which $m_{injection\ group}$ is the mean naked tumor mass of the injection group, and $m_{control\ group}$ is the mean naked tumor mass of the normal control group. All of the experimental data are analyzed using SPSS 18.0 statistical software. Statistical method adopts variance analysis with $p<0.05$, * represents that there is a significant difference as compared with the control group; and for $p<0.01$, ** represents that there is a very significant difference as compared with the control group.

The particular results are shown in Table 2 and Table 3.

Table 2 shows that there are no significant differences among the volumes of tumor in vivo of individual groups of colorectal cancer model mice at the beginning of the experiment ($P>0.05$). Ad-miR-145 and Ad-miR-143 are overexpressed in the bodies of the colorectal cancer model mice after tail vein injection, and at the end of the experiment, as compared with Ad-control group and control plasmid group, the volumes of the tumor in vivo of Ad-miR-145 group and Ad-miR-143 group mice are significantly reduced, with the respective volumes being 56% and 53% of that of the Ad-control group; and the growth rates thereof are significantly lowered, with the respective growth rates being 55% and 51% of that of the Ad-control group. pAd-miR-145 and pAd-miR-143 are overexpressed in the bodies of the colorectal cancer model mice after tail vein injection, and at the end of the experiment, the volumes of the tumors in the bodies of pAd-miR-145 group and pAd-miR-143 group mice are significantly reduced, with the respective volumes being 56% and 55% of that of the control plasmid group; and the growth rates thereof are significantly lowered, with the respective growth rates being 54% and 52% of that of the control plasmid group. The results show that the tumors of model mice can be lessened and the growth rate thereof is reduced through the overexpression of miR-145 and miR-143 in the bodies of colorectal cancer model mice via tail vein injection, thus effectively inhibiting tumor growth and improving the pathological conditions of the focus.

Table 3 shows that Ad-miR-145 and Ad-miR-143 are overexpressed in the bodies of the colorectal cancer model mice via tail vein injection, and at the end of the experiment, as compared with the control group, both the volumes of the naked tumors and the mean tumor weight in the bodies of administration group mice are significantly reduced, with the respective volumes of naked tumors of Ad-miR-145 and Ad-miR-143 groups being 67% and 69% of that of the Ad-control group, and the mean tumor weight thereof being 51% and 47% of that of the Ad-control group. pAd-miR-145 and pAd-miR-143 are overexpressed in the bodies of the colorectal cancer model mice after tail vein injection, both the volumes of the naked tumors and the mean tumor weight in the bodies of administration group mice are significantly reduced, with the respective volumes of naked tumors of pAd-miR-145 and pAd-miR-143 groups being 77% and 71% of that of the control plasmid group, and the mean tumor weight thereof being 55% and 56% of that of the control plasmid group. The tumor inhibition rate in mice is significantly higher than that of the control group. Meanwhile, all of the tumor inhibition rates of the Ad-miR-145 group, the Ad-miR-143 group, the pAd-miR-145 group, and the pAd-miR-143 group are in the range of 49%-67%, and so all of the inhibition effects are quite significant. The results show that miR-145 and miR-143 are overexpressed in the bodies of colorectal cancer model mice after tail vein injection, and as compared with the control group, the tumor volumes of the administration group mice can be lessened and the tumor weights be lightened, thus effectively inhibiting tumor growth and improving the pathological conditions of the focus.

In conclusion, the results of this example show that said functional microRNA is delivered to a focus site through blood circulation, and regulates the physiological/pathological changes in vivo, thereby achieving the effect of treating a disease at the focus site.

TABLE 2 effects on the volumes and growth rates of tumors in vivo in colorectal cancer model mice for individual groups

| Group | N | V0/mm3 | V1/mm3 | VGR/ (mm3 · d −1) |
|---|---|---|---|---|
| Normal | 10 | 14.50 ± 1.10 | 402.65 ± 98.10 | 27.73 ± 5.13 |
| Control plasmid | 10 | 14.40 ± 1.15 | 413.86 ± 76.65 | 29.10 ± 4.21 |
| Ad-control | 10 | 14.43 ± 1.12 | 394.52 ± 66.32 | 27.00 ± 3.24 |
| Ad-miR-145 | 10 | 14.53 ± 2.13 | 224.33 ± 45.47** | 14.99 ± 3.98** |
| Ad-miR-143 | 10 | 14.65 ± 2.09 | 210.33 ± 65.31** | 13.98 ± 2.99** |
| pAd-miR-145 | 10 | 14.45 ± 1.17 | 234.52 ± 56.09** | 15.72 ± 4.12** |
| pAd-miR-143 | 10 | 14.56 ± 1.16 | 229.12 ± 46.11** | 15.33 ± 3.11** |

TABLE 3 effects on the volumes and tumor inhibition rates of naked tumors in naked colorectal cancer model mice for individual groups

| Group | N | $V_{naked\ tumor}$/mm³ | $m_{mean\ tumor\ weight}$/g | $P_{tumor\ inhibition}$/% |
|---|---|---|---|---|
| Normal | 10 | 241.53 ± 96.10 | 2.65 ± 0.25 | |
| Control plasmid | 10 | 224.40 ± 91.12 | 2.84 ± 0.11 | 0.3 |
| Ad-control | 10 | 231.43 ± 94.15 | 2.59 ± 0.13 | 2.3 |

TABLE 3-continued effects on the volumes and tumor inhibition rates of naked tumors in naked colorectal cancer model mice for individual groups

| Group | N | $V_{naked\ tumor}/mm^3$ | $m_{mean\ tumor\ weight}/g$ | $P_{tumor\ inhibition}/\%$ |
|---|---|---|---|---|
| Ad-miR-145 | 10 | 154.53 ± 32.12** | 1.33 ± 0.09** | 49.8* |
| Ad-miR-143 | 10 | 161.65 ± 42.07** | 1.24 ± 0.07** | 53.2* |
| pAd-miR-145 | 10 | 174.45 ± 51.18** | 1.58 ± 0.06** | 67.7* |
| pAd-miR-143 | 10 | 165.56 ± 41.19** | 1.61 ± 0.05** | 64.6* |

All documents referred to in the present invention are incorporated by reference as if each reference is cited alone as a reference in the present application. In addition, it should be understood that after reading the teachings of the present invention described above, a skilled person in the art can make various changes or modifications of the invention, and these equivalent forms also fall into the scope as defined by the appended claims of the present application.

The invention claimed is:

1. A method for treating a disease in the colorectum of a mammal subject, comprising:
   intravenously administering to the mammal subject a composition comprising a recombinant expression vector that expresses functional microRNA in the mammal subject,
   wherein said functional microRNA is miR-143;
   said recombinant expression vector is adenovirus vector, and;
   the disease is colorectal cancer.

2. A method for regulating expression of a target gene of a functional microRNA in the colorectum of a mammal subject, comprising:
   intravenously administering to the mammal subject a composition comprising a recombinant expression vector that expresses functional microRNA in the mammal subject,
   wherein the functional microRNA is miR-143, and
   said recombinant expression vector is adenovirus vector.

* * * * *